(12) United States Patent
Weiss

(10) Patent No.: US 11,442,123 B2
(45) Date of Patent: Sep. 13, 2022

(54) MAGNETIC RESONANCE IMAGING SYSTEM WITH INFRARED THERMOMETRY SENSORS

(71) Applicant: KONINKLIJKE PHILIPS N.V., Eindhoven (NL)

(72) Inventor: Steffen Weiss, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 832 days.

(21) Appl. No.: 15/532,117

(22) PCT Filed: Nov. 30, 2015

(86) PCT No.: PCT/EP2015/078067
§ 371 (c)(1),
(2) Date: Jun. 1, 2017

(87) PCT Pub. No.: WO2016/087594
PCT Pub. Date: Jun. 9, 2016

(65) Prior Publication Data
US 2017/0269176 A1    Sep. 21, 2017

(30) Foreign Application Priority Data
Dec. 4, 2014   (EP) ..................................... 14196342

(51) Int. Cl.
*G01R 33/28* (2006.01)
*A61B 5/01* (2006.01)
(Continued)

(52) U.S. Cl.
CPC .............. *G01R 33/288* (2013.01); *A61B 5/01* (2013.01); *A61B 5/055* (2013.01);
(Continued)

(58) Field of Classification Search
CPC ............ G01R 33/288; G01R 33/34015; G01R 33/3657; G01R 33/28; G01R 33/3415;
(Continued)

(56) References Cited

U.S. PATENT DOCUMENTS 6,320,379 B1    11/2001  Young
7,301,343 B1 *  11/2007  Sellers .................... G01R 33/28
                                                            324/318
(Continued)

FOREIGN PATENT DOCUMENTS

JP          01293863 A     11/1989
JP           1176195 A      3/1999
(Continued)

OTHER PUBLICATIONS

Ibrahim et al "Evaluation of MRI RF Probes Utilizing Infrared Sensors" IEEE Transactions on Biomedical Engineering, vol. 53, No. 5, May 2006 p. 963-967.
(Continued)

*Primary Examiner* — Catherine B Kuhlman
*Assistant Examiner* — Sean A Frith

(57) ABSTRACT

A magnetic resonance imaging system (100, 300) for acquiring magnetic resonance data (142) from a subject (118) within an imaging zone (108) includes a magnetic resonance imaging antenna (113, 113') comprising having multiple loop antenna elements (114, 114') with multiple infrared thermometry sensors (115, 115'). The magnetic resonance imaging antenna is configured for being positioned adjacent to an external surface (119) of the subject and at least a portion of the multiple infrared thermometry sensors are directed towards the external surface. The magnetic resonance imaging system further includes a memory (134, 136) containing machine executable instructions (150, 152) and pulse sequence instructions (140). The machine executable
(Continued)

instructions causes a processor controlling the system to: acquire (200) the magnetic resonance data by controlling the magnetic resonance imaging system with the pulse sequence instructions; repeatedly (202) measure at least one surface temperature (146) of the subject with the multiple infrared thermometry sensors during acquisition of the magnetic resonance data; and perform (204) a predefined action if the at least one surface temperature is above a predefined temperature.

18 Claims, 8 Drawing Sheets

(51) Int. Cl.
 A61B 5/055 (2006.01)
 G01R 33/34 (2006.01)
 G01R 33/36 (2006.01)
 A61B 5/00 (2006.01)
 G01R 33/3415 (2006.01)

(52) U.S. Cl.
 CPC ... *G01R 33/34015* (2013.01); *G01R 33/3657* (2013.01); *A61B 5/0035* (2013.01); *A61B 2560/0266* (2013.01); *G01R 33/28* (2013.01); *G01R 33/3415* (2013.01); *G01R 33/3685* (2013.01)

(58) Field of Classification Search
 CPC ....... G01R 33/3635; A61B 5/01; A61B 5/055; A61B 5/0035; A61B 2560/0266
 See application file for complete search history.

(56) References Cited

U.S. PATENT DOCUMENTS

| | | | | |
|---|---|---|---|---|
| 8,452,382 | B1* | 5/2013 | Roth | A61B 5/6887 600/309 |
| 8,519,711 | B2 | 8/2013 | Sakakura | |
| 2006/0064002 | A1* | 3/2006 | Grist | A61B 5/015 600/410 |
| 2007/0230767 | A1* | 10/2007 | Iwamatsu | A61B 5/05 382/133 |
| 2009/0215384 | A1* | 8/2009 | Wohlfarth | G01R 33/28 454/258 |
| 2010/0176809 | A1* | 7/2010 | Biber | G01R 33/3692 324/309 |
| 2010/0256480 | A1* | 10/2010 | Bottomley | G01R 33/285 600/411 |
| 2011/0037471 | A1* | 2/2011 | Nozaki | G01R 33/34015 324/322 |
| 2011/0046475 | A1* | 2/2011 | Assif | G01R 33/565 600/422 |
| 2012/0306494 | A1* | 12/2012 | Yang | G01R 33/3664 324/318 |
| 2013/0154642 | A1* | 6/2013 | Sueoka | G01R 33/34015 324/309 |
| 2013/0318693 | A1* | 12/2013 | McBride | A41D 13/1209 2/456 |
| 2014/0015528 | A1* | 1/2014 | Landschuetz | G01R 33/56509 324/309 |
| 2014/0062485 | A1* | 3/2014 | Okamoto | G01R 33/3692 324/322 |
| 2014/0084917 | A1 | 3/2014 | Dewdney | |
| 2014/0125339 | A1* | 5/2014 | Lee | G01R 33/3415 324/319 |
| 2014/0197832 | A1* | 7/2014 | Driesel | H01Q 7/005 324/307 |
| 2014/0361769 | A1* | 12/2014 | Hardie | G01R 33/3692 324/307 |
| 2015/0265856 | A1 | 9/2015 | Hill | |

FOREIGN PATENT DOCUMENTS

| | | | |
|---|---|---|---|
| JP | 2008212437 A | 9/2008 | |
| JP | 2009005759 A | 1/2009 | |
| JP | 2009183472 A | 8/2009 | |
| WO | WO-2013054231 A2 * | 4/2013 | ............ G01R 33/28 |

OTHER PUBLICATIONS

Homann H, Graesslin I, Eggers H, Nehrke K, Vernickel P, Katscher U, Dössel O, Börnert P. Local SAR management by RF shimming: a simulation study with multiple human body models. Magn Reson Mater Phys 2012;25:193-204.

Luechinger R, et al. In vivo heating of pacemaker leads during magnetic resonance imaging. Eur Heart J 2005:26,376-383.

\* cited by examiner

MAGNETIC RESONANCE IMAGING SYSTEM WITH INFRARED THERMOMETRY SENSORS

CROSS REFERENCE TO RELATED APPLICATIONS

This application is a U.S. national phase application of International Application No. PCT/EP2015/078067, filed on Nov. 30, 2015, which claims the benefit of EP Application Serial No. 14196342.1 filed on Dec. 4, 2014 and is incorporated herein by reference.

TECHNICAL FIELD OF THE INVENTION

The invention relates to magnetic resonance imaging, in particular to apparatus and methods for preventing the overheating of a subject during magnetic resonance imaging.

BACKGROUND OF THE INVENTION

A static magnetic field is used by Magnetic Resonance Imaging (MRI) scanners to align the nuclear spins of atoms as part of the procedure for producing images within the body of a patient. This static magnetic field is referred to as the $B_0$ field. It is commonly known that increasing the strength of the $B_0$ field used for performing an MRI scan offers the opportunity of increasing the spatial resolution and contrast resolution of the diagnostics images. This increase in resolution and contrast benefits physicians using an MRI image to diagnose a patient.

During an MRI scan, Radio Frequency (RF) pulses generated by a transmitter coil cause perturbations to the local magnetic field. These perturbations are known as the $B_1$ field. The $B_1$ field is used to manipulate the orientation of the nuclear spins. These RF signals are used to construct the MRI images. These coils can also be referred to as antennas. Further, the transmitter and receiver coils can also be integrated into a single transceiver coil that performs both functions. It is understood that the use of the term transceiver coil also refers to systems where separate transmitter and receiver coils are used. A difficulty is that the B1 field can also cause heating of the subject being imaged. To image regions deep within the body of a subject, the surface regions of the subject can be exposed to levels of radiation which can overheat tissue. The term Specific Absorption Ratio (SAR) is the radio frequency power absorbed per unit mass in tissue and is a measure of this overheating.

European patent application EP 0 841 576 D1 specification discloses a probe designed to be inserted into and removed from a patient that carries at least one sensor used for control the target of energy related to an interventional procedure. In the Japanese patent application JP2008-212437. an RF transmission coil with a decoupling circuit is disclosed. The decoupling circuit is provided with a temperature sensor. The high-frequency irradiation is stopped when the temperature exceeds a predetermined threshold.

SUMMARY OF THE INVENTION

The invention relates to a magnetic resonance imaging system, a method of operating a magnetic resonance imaging system and a magnetic resonance imaging antenna in independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for magnetic resonance imaging systems requiring magnetic resonance data from a subject within an imaging zone. The magnetic resonance imaging system comprises a magnetic resonance imaging antenna comprising multiple loop antenna elements. The magnetic resonance imaging antenna further comprises multiple infrared thermometry sensors. Notably, an individual infrared thermometry sensors may be associated with one of the antenna elements; such an antenna element is formed as a conductor loop for transmitting a radio frequency field or for receiving radio frequency magnetic resonance signals. For example, each infrared thermometry sensor may be associated with one of the antenna loops. An infrared thermometry sensor as used herein encompasses a sensor which can measure temperature by using infrared radiation. The magnetic resonance imaging antenna is configured for being positioned adjacent to an external surface of the subject. At least a portion of the multiple infrared thermometry sensors are directed towards the external surfaces when the magnetic resonance imaging antenna is positioned adjacent to the external surface of the subject. An alternative way of wording this is that the magnetic resonance imaging antenna has an outer surface and that the multiple infrared thermometry sensors are able to measure the surface temperature of objects adjacent to the outer surface.

The magnetic resonance imaging system further comprises a memory containing machine executable instructions and pulse sequence instructions. Pulse sequence instructions as used herein encompass commands or a sequence of events such as events in a timeline which can be converted into commands; they may be used to control the magnetic resonance imaging system to acquire the magnetic resonance data according to a magnetic resonance imaging technique. The magnetic resonance imaging system further comprises a processor for controlling the magnetic resonance imaging system. Execution of the machine executable instructions causes the processor to acquire the magnetic resonance data by controlling the magnetic resonance imaging system with the pulse sequence instructions. Execution of machine executable instructions further causes the processor to repeatedly measure at least one surface temperature of the subject with the multiple infrared thermometry sensors during acquisition of the magnetic resonance data. Alternatively this may be worded in that the machine executable instructions cause the processor to repeatedly measure at least one temperature with the multiple infrared thermometry sensors during acquisition of the magnetic resonance data.

Execution of the machine executable instructions further causes the processor to perform a predefined action if at least one surface temperature is above a predefined temperature. If at least one of the multiple infrared thermometry sensors measures a temperature which is above the predefined temperature then the processor takes a specific or predefined action. This example may have the benefit that the magnetic resonance imaging system can react automatically to heating caused by the acquisition of magnetic resonance data. That is the action taken by the processor achieves to reduce the risk of the subject becoming overheated.

In another example the antenna could be a send and/or a receive antenna. That is to say the antenna may be in some instances used for receiving magnetic resonance data and in other instances may be used for transmitting radio frequency pulses for manipulating spins of the subject within the imaging zone.

In another embodiment each of the multiple loop antennas have current leads. A current lead as used herein is a point on the antenna where radio frequency current is fed into or received from the multiple loop antenna element. At least a subset of the multiple infrared thermometry sensors is positioned in an offset region. The current leads are within the offset region. The offset region may alternatively be defined or described as a region of each of the multiple loop antennas which is near or adjacent to the current leads. It may be beneficial to place the multiple infrared thermometry sensors at the position for the current leads because the voltage or the area with the largest electric fields may be near the location of the current leads. If the antenna is a transmit antenna it may be expected that the heating of the subject by the magnetic resonance imaging antenna would be near to the regions where the current leads are.

In another embodiment each of the multiple loop antennas have current leads. The current leads as used herein are commonly interrupted by capacitors. At least a subset of the multiple infrared thermometry sensors is positioned next to the current leads. It may be beneficial to place the multiple infrared thermometry sensors at the position of the capacitors because the voltage or the area with the largest electric fields may alternatively be near the location of the capacitors. If the antenna is a transmit antenna it may be expected that the heating of the subject by the magnetic resonance imaging antenna would be near to the regions where the capacitors are.

In another embodiment the magnetic resonance imaging antenna is configured for functioning as a transmit antenna. For example, the magnetic resonance imaging antenna may be connected to a transmitter or a transceiver. The magnetic resonance imaging system comprises a radio frequency system for supplying radio frequency power to each of the subset of multiple antenna elements. The predefined action comprises reducing the radio frequency power supplied to an antenna element if an infrared thermometry sensor in the offset region of the loop antenna element measures a surface temperature above the predefined temperature. The infrared thermometry sensor is chosen from the subset of the multiple infrared thermometry sensors. The loop antenna element is chosen from the subset of multiple antenna elements. In this example, the surface temperature is measured adjacent to a particular loop antenna element. If the surface temperature of the subject is above the threshold then the radio frequency system can automatically reduce the power supplied to that particular loop antenna element thus reducing the heating of the subject.

In some examples the RF power is reduced by either changing a flip angle of the imaging sequence which is in the full sequence instructions or by relaxing or pausing the time regime of the pulse sequence.

In another embodiment, at least a portion of the multiple infrared thermometry sensors are each positioned in a central region of a loop antenna element chosen from the multiple loop antenna elements.

The multiple infrared thermometry sensors positioned in the central region may be used in the same way as the infrared thermometry sensors, which are positioned in an offset region that is next to the current leads and/or capacitors. For example if the loop antenna element measures too high of a surface temperature this may then also cause the radio frequency system to reduce the power supplied to the loop antenna element which the infrared thermometry sensor is closest to.

In another embodiment the magnetic resonance imaging antenna is configured for functioning as a receive antenna. For example the magnetic resonance imaging antenna may be connected to a receiver or a transceiver.

In another embodiment the magnetic resonance imaging antenna comprises a subject support configured for supporting the subject on a support surface at least partially within the imaging zone. At least a portion of the antenna elements are arranged within the subject support and adjacent to the support surface. In this example at least a part of the magnetic resonance imaging antenna is built into the subject support. Incorporating the antenna elements with the infrared thermometry sensors into the subject support may have the benefit that it reduces the chances of the subject being overheated during the acquisition of magnetic resonance data.

In another embodiment the magnetic resonance imaging antenna comprises a flexible surface antenna. The flexible surface antenna is configured for being placed in contact with a portion of outer surface of the subject. In this example at least a part of the magnetic resonance imaging antenna is a flexible antenna which can be placed over or about the subject. The use of the infrared thermometry sensors may be beneficial because it is difficult to have direct contact with the antenna and the subject. Using the infrared thermometry sensors enables the antenna to be used and accurately measure the temperature of the subject without being in physical contact.

In another embodiment the magnetic resonance imaging system comprises an air cooling system for cooling the subject within the imaging zone with an airflow. The predefined action comprises increasing airflow if the surface temperature is above the predefined temperature.

In another embodiment execution of the machine executable instructions further causes the processor to select the predefined temperature from a table of predefined temperatures using any one of the following criterion or criteria: subject weight, subject age, subject type, subject size, and combinations of thereof.

The use of such a criterion may be useful because models can be developed using empirical data or modeled information.

In another embodiment the predefined action is the halting of the acquisition of the magnetic resonance data. In this embodiment the predefined action is to break off the acquisition of magnetic resonance data In another embodiment the predefined action is the modification of the pulse sequence instructions. This for instance may cause a particular loop antenna element to have its power reduced, the particular phase or flip angle sent to it, or even pauses during the acquisition of the magnetic resonance data. That, the pausing means that acquistion of magnetic resonance data is interruped temporarilty, until the surface temperature may fall below the predefined temperature, or oven below a safety margin below the predefined temperature.

In another embodiment the predefined action is the increase of the air ventilation to a subject to increase cooling.

In another embodiment the predefined action is the pausing or delaying of the acquisition of the magnetic resonance data.

In another aspect, the invention provides for a method of operating a magnetic resonance imaging system requiring magnetic resonance data from a subject within an imaging zone period. The magnetic resonance imaging system comprises a magnetic resonance imaging antenna comprising multiple antenna elements. Each of the antenna elements is a loop antenna element. The magnetic resonance imaging antenna further comprises multiple infrared thermometry sensors. The magnetic resonance imaging antenna is configured for being positioned adjacent to an external surface of the subject. At least a portion of the multiple infrared thermometry sensors are directed towards the external surface when the magnetic resonance imaging antenna is positioned adjacent to the external surface. The method comprises of the steps of acquiring the magnetic resonance data by controlling the magnetic resonance imaging system with pulse sequence instructions. The method further comprises the step of repeatedly measuring a surface temperature of the subject with each of the multiple infrared thermometry sensors during acquisition of the magnetic resonance data. The method comprises of performing a predefined action if the surface temperature is above a predefined temperature.

In another embodiment, the method further comprises placing an infrared transparent garment on the outer surface on the subject before acquiring the magnetic resonance data. This may be beneficial because the infrared sensors are used to measure the surface temperature of the subject. If the subject is wearing a normal garment then the fabric or material of the garment may block the measurement of the surface temperature of the subject. Using an infrared transparent garment or one with a high infrared transparent transmissivity may enable the measurement to be made even if the subject is wearing a garment.

In another embodiment, the infrared transparent garment is fabricated at least partially from polyethylene foil. The use of polyethylene foil to manufacture the infrared transparent garment may be beneficial because polyethylene foil has a high degree of transmission of infrared light.

In another example the invention provides for a magnetic resonance imaging antenna comprising multiple antenna elements. Each of the antenna elements is a loop antenna element. The magnetic resonance imaging antenna further comprises multiple infrared thermometry sensors. The magnetic resonance imaging antenna is configured for being positioned adjacent to an external surface of the subject. At least a portion of the multiple infrared thermometry sensors are directed towards the external surface when the magnetic resonance imaging antenna is positioned adjacent to the external surface.

In another embodiment the magnetic resonance imaging antenna is integrated into a subject support.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
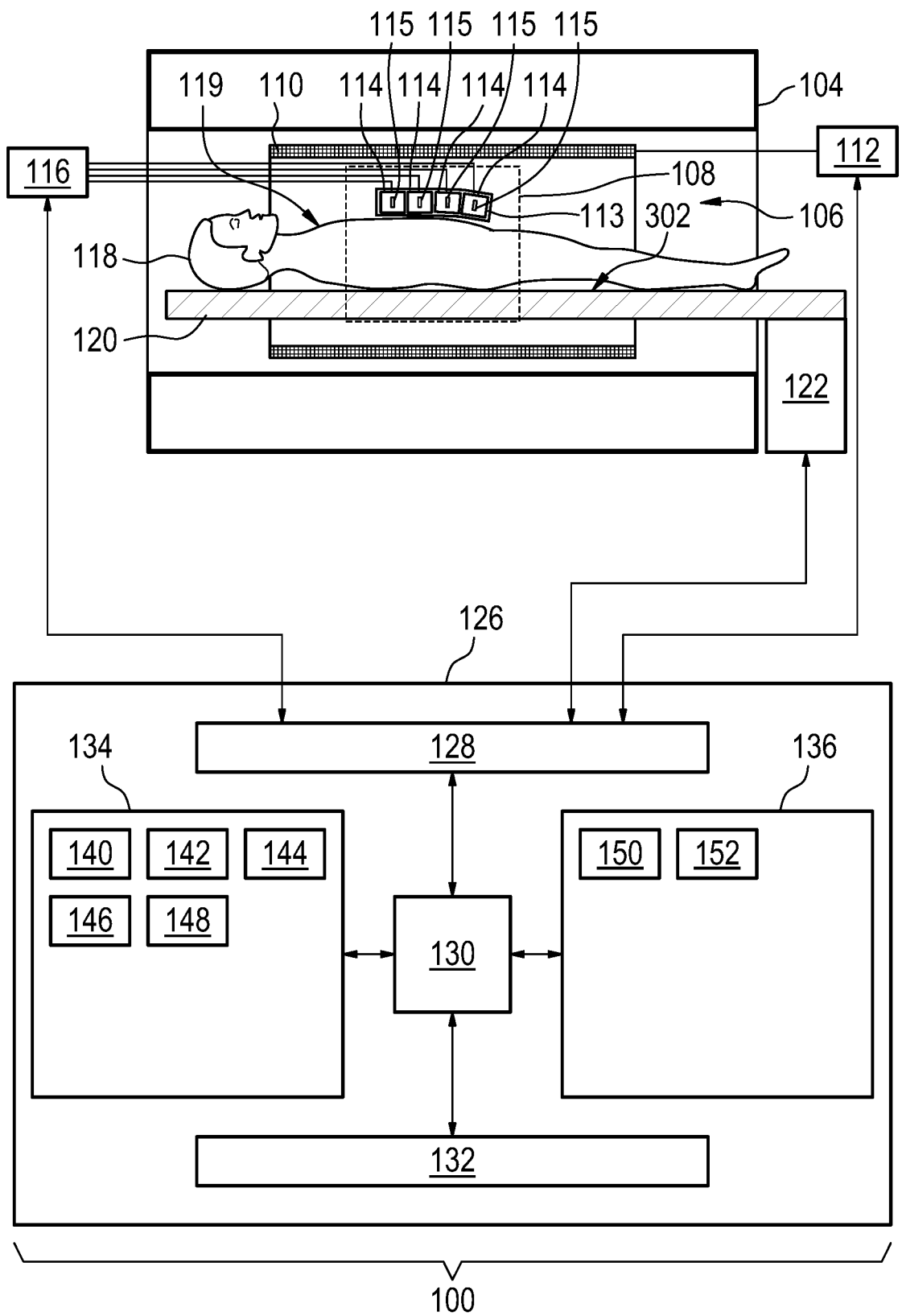
FIG. 1 illustrates an example of a magnetic resonance imaging system.

FIG. 1 shows an example of a magnetic resonance imaging system 100 with a magnet 104. The magnet 104 is a superconducting cylindrical type magnet 104 with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a magnetic resonance antenna 113 for manipulating the orientations of magnetic spins within the imaging zone 108 and for receiving radio transmissions from spins also within the imaging zone 108. The radio frequency antenna contain multiple coil elements 114. The radio frequency antenna may also be referred to as a channel or antenna. The magnetic resonance antenna 113 is connected to a radio frequency transceiver 116. The magnetic resonance antenna 113 and radio frequency transceiver 116 may be replaced by separate transmit and receive coils and a separate transmitter and receiver. It is understood that the magnetic resonance antenna 113 and the radio frequency transceiver 116 are representative. The magnetic resonance antenna 113 may also represent a dedicated transmit antenna and a dedicated receive antenna. Likewise the transceiver 116 may also represent a separate transmitter and receivers. The magnetic resonance antenna 113 may also have multiple receive/transmit elements and the radio frequency transceiver 116 may have multiple receive/transmit channels. The transmit antenna may also be built into the bore of the magnet in a layer beneath (more central) to the gradient coil.

The subject support 120 is attached to an optional actuator 122 that is able to move the subject support and the subject 118 through the imaging zone 108. The transceiver 116, the magnetic field gradient coil power supply 112 and the actuator 122 are all see as being connected to a hardware interface 128 of computer system 126.

The subject 118 can be seen as having a magnetic resonance antenna 113 placed on an outer surface 119 of the subject 118. The magnetic resonance imaging antenna 113 is made up of a number of loop antenna elements 114. Also shown is an infrared thermometry sensor 115 that is associated with each of the loop antenna elements 114. These infrared thermometry sensors 115 may be used to measure a surface temperature on the outer surface 119.

The computer storage 134 is shown as containing pulse sequence instructions 140 for performing a magnetic resonance fingerprinting technique. The computer storage 134 is further shown as containing magnetic resonance data 142 that was acquired using the pulse sequence instructions 140 to control the magnetic resonance imaging system 100. The computer storage is further shown as containing a magnetic resonance image 144 that was reconstructed using the magnetic resonance data 142. The computer storage 134 is further shown as containing thermometry data 146 as measured using the infrared thermometry sensors 115. The computer storage 134 is further shown as containing a predefined temperature or a temperature model which returns a predefined temperature 148. The predefined temperature for example 148 may be used to compare against the thermometry data 146 to determine if the outer surface 119 of the subject 118 is too hot or warm.

The computer memory 136 contains a control module 150 which contains such code as operating system or other instructions which enables the processor 130 to control the operation and function of the magnetic resonance imaging system 100.

The computer memory 136 is further shown as containing an image reconstruction module 152 that uses the magnetic resonance data 142 to reconstruct the magnetic resonance image 144.

Figure 2:
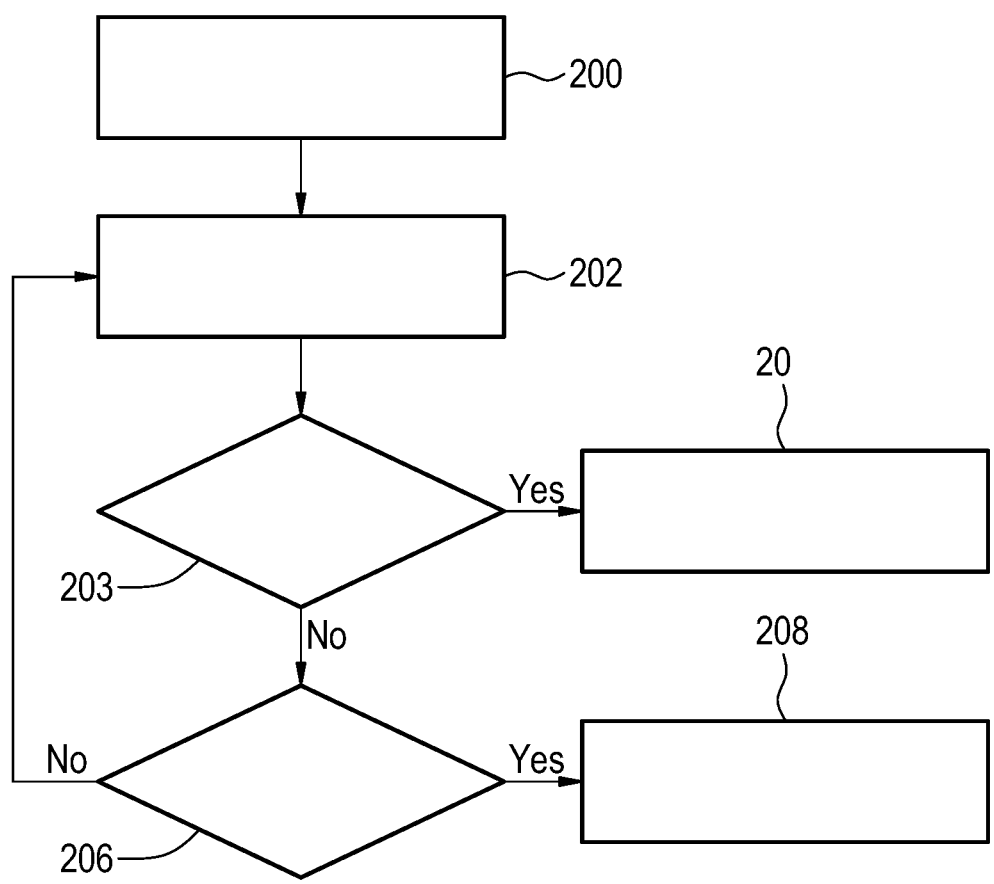
FIG. 2 shows a flow chart that illustrates a method of operating the magnetic resonance imaging system of FIG. 1.

FIG. 2 shows a flow chart which illustrates a method of operating the magnetic resonance imaging system 100 of FIG. 1. First in step 200, the magnetic resonance data 142 is acquired by controlling the magnetic resonance imaging system 100 with the pulse sequence instructions 142. Next in step 202, the processor 130 measures at least one surface temperature with the infrared thermometry sensors 115. This is stored as thermometry data 146 in the computer storage 134. The next step is a decision box with the question: is a measured surface temperature above the predefined temperature? If yes, then the method proceeds to step 204. If no, then the method proceeds to step 206. In step 204, the processor 130 performs a predefined action if the thermometry data 146 or at least one surface temperature is above a predefined temperature 148. Step 206 is another decision box. The question for box 206 is: Is the acquisition of magnetic resonance data finished. If yes, the method proceeds to step 208. In step 208 the method ends. If the answer to the question of box 206 isno, then the method returns to step 202 where the at least one surface temperature is measured with the infrared thermometry sensors again.

Figure 3:
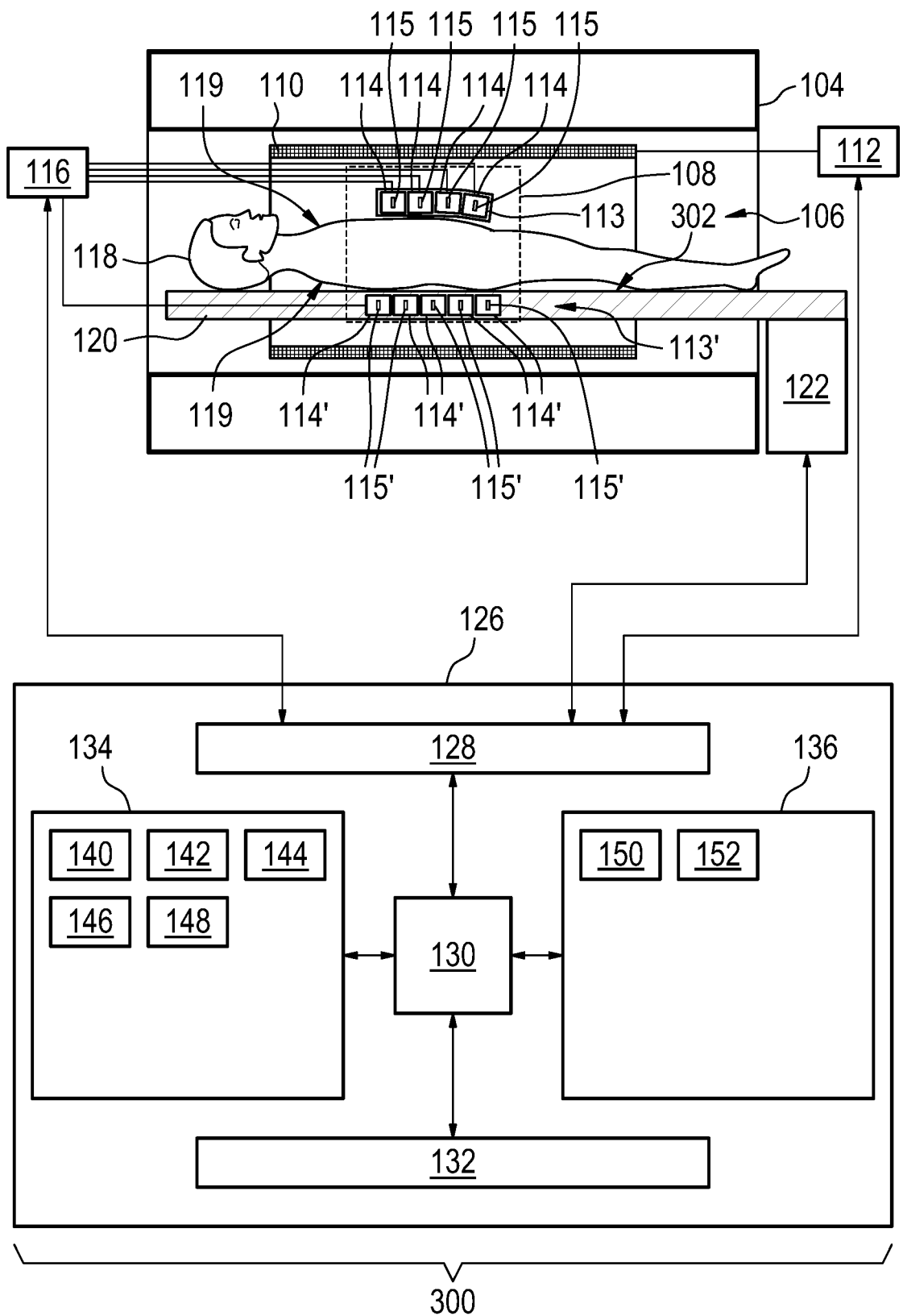
FIG. 3 illustrates a further example of a magnetic resonance imaging system.

FIG. 3 illustrates a further example of a magnetic resonance imaging system 300. The magnetic resonance imaging system 300 is similar to that shown in FIG. 1 with the addition of several additional features. In this example additional magnetic resonance imaging antenna 113' embedded in the subject support 120. The subject support has a support surface 302 and there are a number of loop antenna elements 114' adjacent to the supporting surface 302. There are also a number of infrared thermometry sensors 115' which are exposed to the underside of the subject 118. This enables a further measuring of the surface temperature on the outer surface 119 of the subject 118.

Figure 4:
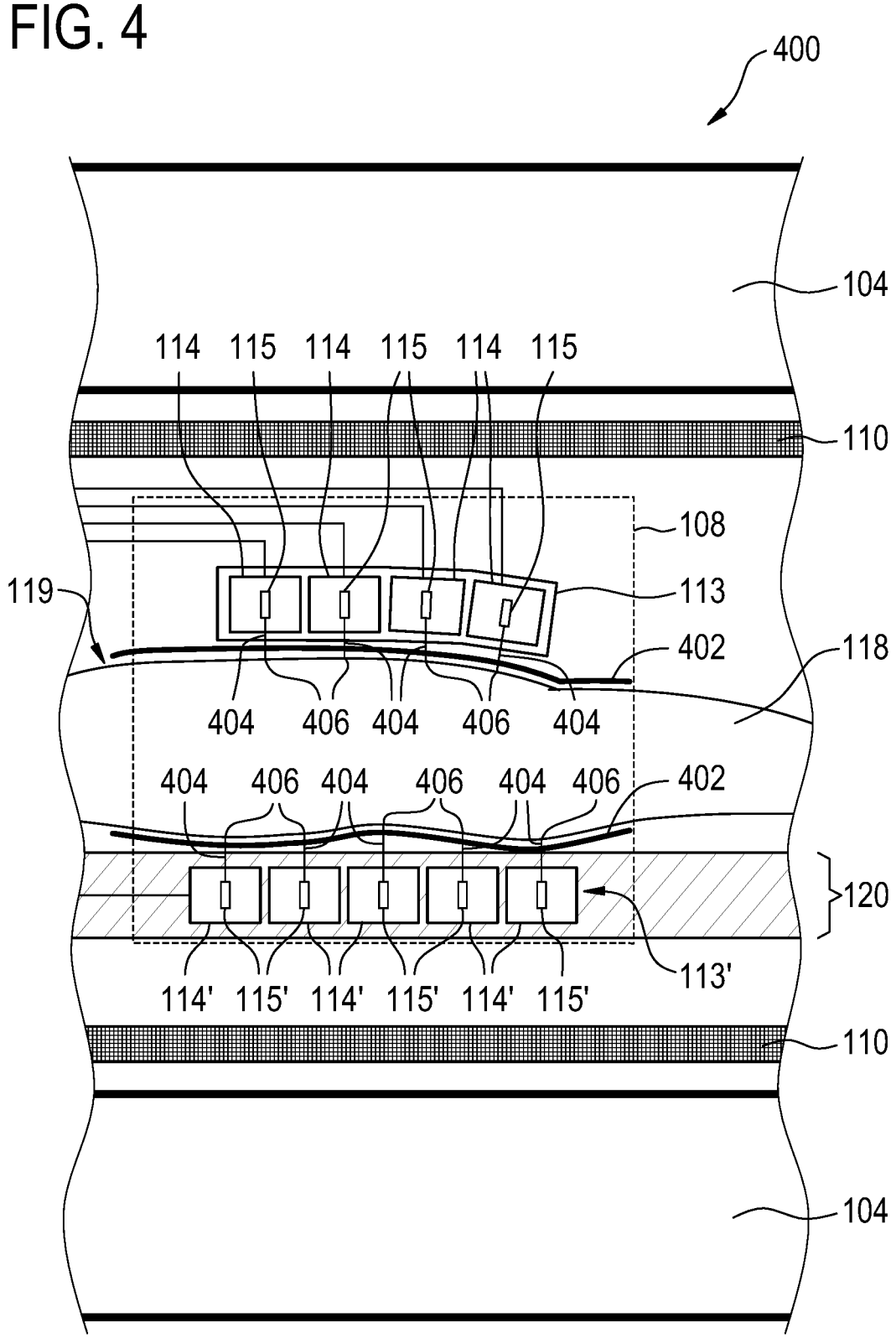
FIG. 4 shows an enlarged view of a portion of FIG. 3.

FIG. 4 shows an enlarged view 400 of the imaging zone 108 shown in FIG. 3. In this example there is an infrared transparent garment 402 between the infrared thermometry sensors 115, 115' and the outer surface 119 of the subject 118. The infrared transparent garment 402 enables the sensors 115, 115' to still take temperature measurements of the outer surface 119 of the subject 118. For example each of the infrared thermometry sensors 115, 115' has a line labeled 404 which shows where the sensor 115, 115' is aimed at a measurement point 406 on the surface 119 of the subject 118. It can be seen how using a large number of these sensors enables a large number of measurement points 406 where the thermometry data 146 can be acquired. It can also be seen how both magnetic resonance imaging antennas 113 and 113' do not conform to the outer surface 119 of the subject 118. However because infrared thermometry sensors 115, 115' are used it is still possible to make accurate temperature measurements at the measurement points 406.

Figure 5:
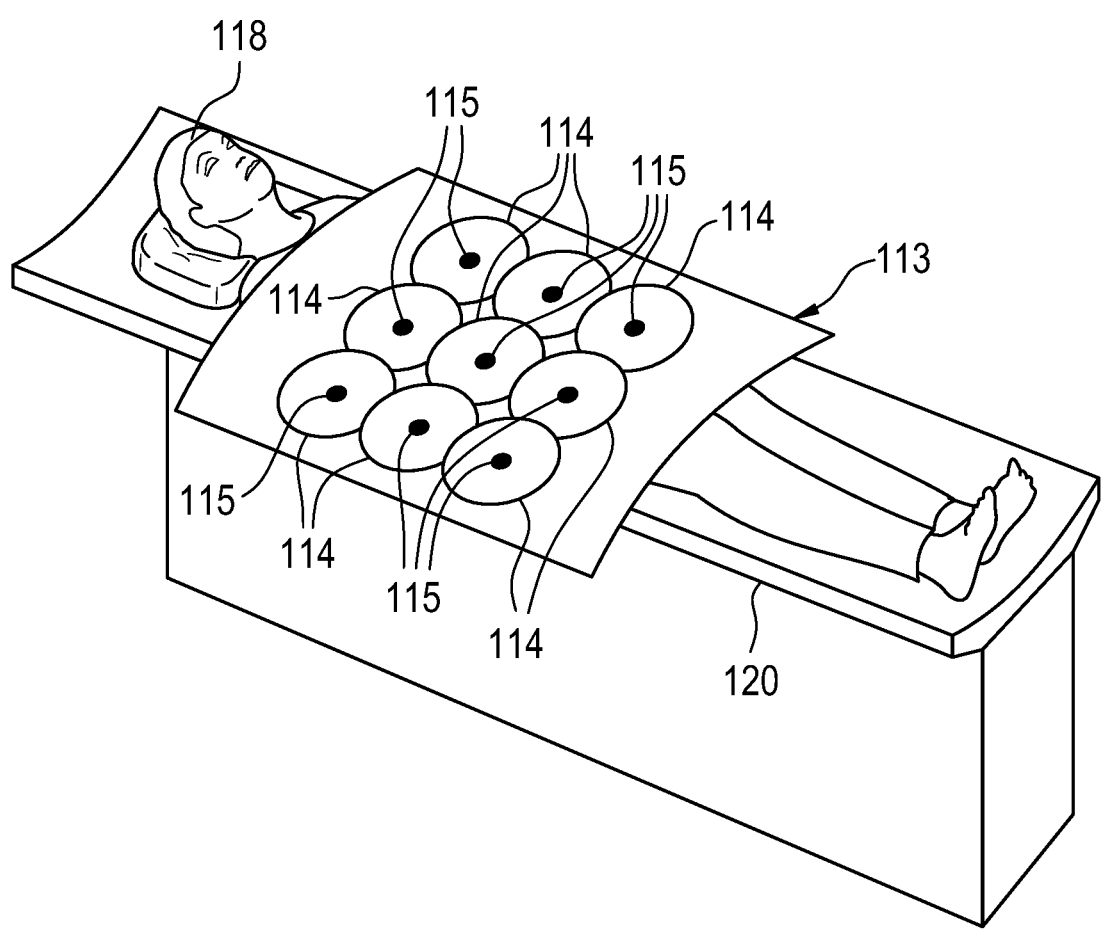
FIG. 5 illustrates an example of a magnetic resonance imaging antenna.

FIG. 5 shows an alternative view of the subject 118 reposing on the subject support 120 with the magnetic resonance antenna 113 draped over the subject 118.

Figure 6:
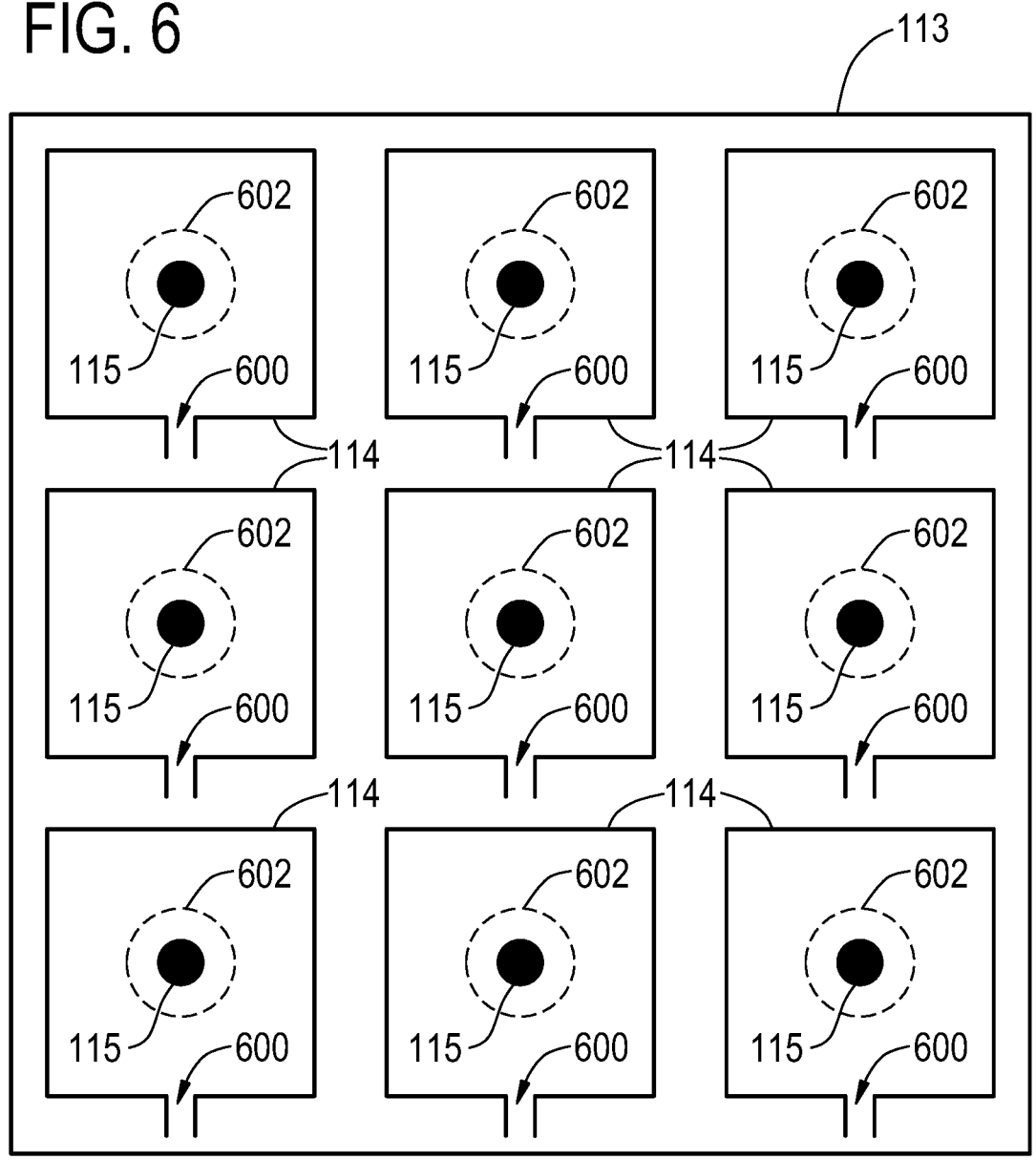
FIG. 6 illustrates a further example of a magnetic resonance imaging antenna.

FIG. 6 shows an alternative way of laying out the antenna elements 114 and infrared thermometry sensors 115. In this example each of the loop antenna elements 114 has a set of current leads 600 which may be either used for either supplying RF current to the loop antenna 114 or for receiving a radio frequency signal from the loop antenna elements 114. Each loop antenna element 114 has a central region 602 where the infrared thermometry sensor 115 is placed. Variations of the design shown in FIG. 6 may also be made. For example it is very common for the loop antenna elements 114 to be partially overlapping.

Figure 7:
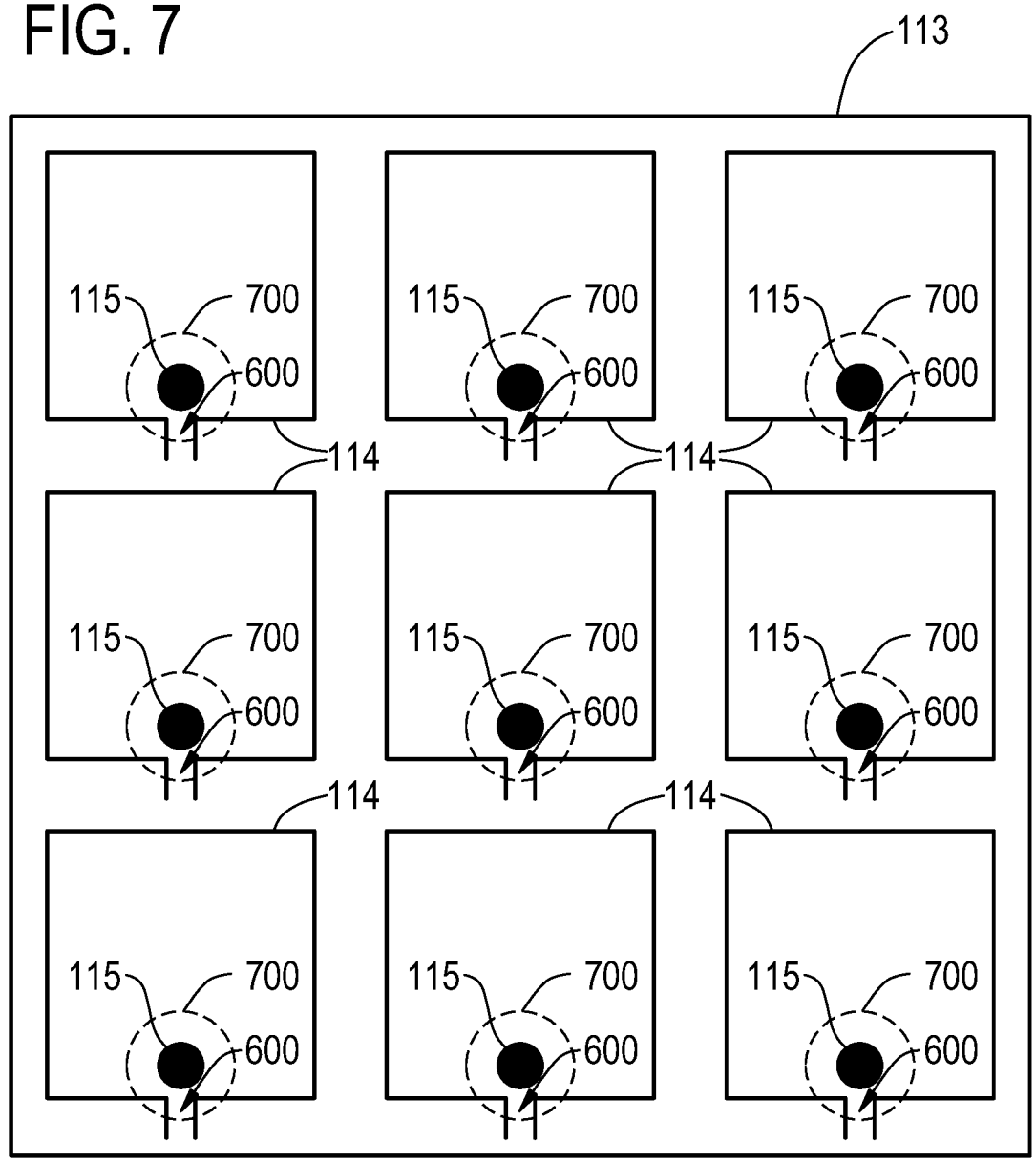
FIG. 7 illustrates a further example of a magnetic resonance imaging antenna.

FIG. 7 shows a further modification of the design shown in FIG. 6. In this example the infrared thermometry sensors 115 are placed within an offset region 700. The offset region 700 is away from the central region and encompasses the region which contains the current leads 600. When an RF voltage or a current is applied to the current lead 600 there may be a larger electric field in that vicinity. It may therefore be beneficial for a transmit antenna to place infrared thermometry sensors 115 in this offset region 700.

Figure 8:
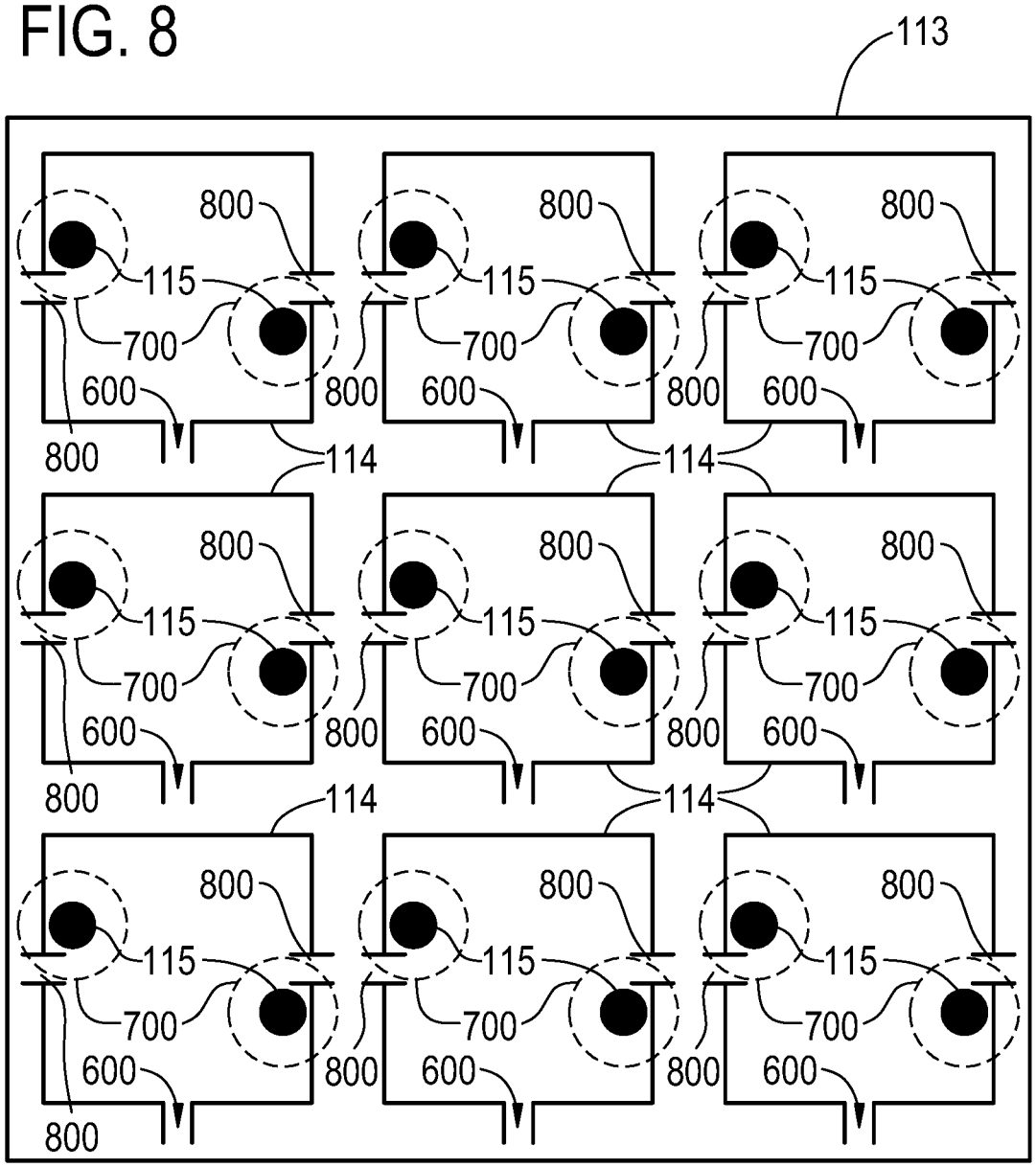
FIG. 8 illustrates a further example of a magnetic resonance imaging antenna.

FIG. 8 shows a further modification of the design shown in FIG. 7. In this example the antenna elements 114 also have capacitors 800. The offset region 700 in this example is positioned near the capacitors. The infrared thermometry sensors 115 are again placed within the offset region 700. The offset region 700 is away from the central region and encompasses the region which contains the capacitors 800. Shown in the figure are two capacitors per antenna element 114. There is an offset region 700 near each capacitor and a infrared thermometry sensor 115 in each of the offset regions 700. The example in FIGS. 7 and 8 are intended to provide an example. The positioning of the current leads and any reactive components such as capacitors will vary depending upon the design of the magnetic resonance antenna. The infrared thermometry sensors 115 can be placed near portions of the antenna elements where larger heating of the subject is to be expected.

The trend towards higher field strength, shorter scan times, and the upcoming trend towards surface transmit coil arrays has increased the risk of local SAR hotspots in superficial tissue. Examples may integrate multiple Infra Red (IR) thermometers into MR surface (receive or transmit/ receive) coil arrays and to monitor the surface temperature during scanning at multiple points.

The SAR model/simulations may be used to optimize the sequences while keeping SAR values in allowable limits. Such models and simulations may for example be updated such as to match or fit with the actual temperature measurements.

In case of inacceptable MRI-induced heating several countermeasures or predetermined actions may be performed:

The MR sequence is modified to provide reduced overall SAR

Air ventilation is increased

Local SAR is reduced by adjusting transmit powers for individual coil elements of the transmit coil As mentioned above, the trend towards higher field strength, shorter scan times, and the upcoming trend towards surface transmit coils has increased the risk of local SAR hotspots in superficial tissue. SAR becomes frequently the limitation for even faster image acquisition. SAR management has been introduced to address this fact using $B_1$ measurements, SAR and temperature simulations and Bi shimming to keep local SAR below allowable limits.

SAR often represents the limiting factor for faster exams. Multi-element system body coils and surface transmission coils are subject of research with the aim to increase the degrees of freedom for SAR management via $B_1$ shimming, but such coils are also prone to causing superficial SAR that is not easy to predict per simulation.

Measuring $B_1$ and SAR via temperature mapping as preparation steps for the planned exam are causing considerable increase of exam times. This problem would become even larger for multi-element transmit coils covering a large fraction of the patient, because scan times would become extremely large.

Simulation of SAR and temperature are computationally intense and require additional scans to provide a patient specific model (including anatomy, electrical properties, and thermal properties). In addition, simulations are associated with error margins.

The SAR limits for clinical scanning themselves include safety margins because of the imperfections in SAR monitoring, and SAR models of the MR systems also include safety margins for the same reason. Such margins limit exam times more than actually required. A better knowledge of actual temperatures during scanning may allow lowering those margins.

Examples may integrate infrared thermometry sensors or multiple IR thermometers into MR surface (receive or transmit/receive) coil such that they look onto the patient such as is shown in FIG. 4. IR sensors are available in dimensions of 1-2 cm that allow integration into standard coil arrays. Sensors with a cost price of about 5 USD are available that allow integration of multiple sensors e.g. on a grid pattern of 10 cm spacing without increasing the cost price of the coil considerably.

IR sensors are used to maintain a smooth workflow of the examination. This would not be possible with contact temperature sensors which would need to be fixated on the skin to achieve a stable thermal contact. The IR radiation emitted by the human skin in the suitably detectable range (2-20 µm) originates not only directly from the surface of the skin but also from a layer of superficial tissue of about 1 mm, hence effectively the temperature of that layer is measured.

Special IR transparent clothes for the patient may also be fabricated, which are mostly IR transparent in the range of the detected radiation.

The main components of IR pyrometer are non-conductive and non-ferromagnetic: IR window, IR lens, thermocouple sensor with wires (made from e.g. copper, constantan, chromel, nicrosil, nisil, Rhodium, Platinum, PtRh). Devices with plastic housings are available (see below). It is possible to use thermocouples equipped with shielded wires to measure MRI-induced heating. Connective wires have to be shielded and probably equipped with common-mode current traps as it is state-of-the-art in wiring of the MR receive elements themselves.

The temperature is expected to rise after application of the surface coil and introduction of the patient into the bore. However, this temperature should relatively quickly approach a steady state. Residual baseline drifts that are present short shortly before scanning are determined and corrected. MRI-induced temperature increases may be monitored in real-time during scanning and temperature data is fed into the MR host computer.

In general, any simulations that have been performed before the scan as part of the SAR model that is used to optimize the sequence are updated such as to comply with the actual temperature. If the grid of temperature readings across the patient is sufficiently dense, the absence of relevant MR induced heating may be used to recalculate the current and subsequent sequences to shorten the acquisition time.

In case of inacceptable MRI-induced heating several countermeasures can be performed, initiated and controlled by the MR host computer:

The MR sequence is modified to provide reduced overall SAR

Air ventilation is increased

Local SAR is reduced by adjusting transmit powers for individual coil elements of the transmit coil.

Advances in electronic and detector technology have resulted in a variety of non-contact IR thermometers for industrial and scientific use. IR detectors fall into two main groups: quantum detectors and thermal detectors (pyrometers). Quantum detectors are semiconductors that interact directly with the impacting photons, resulting in electron pairs and therefore an electrical signal. Thermal detectors change their temperature depending upon the impacting radiation which is then detected mostly by a thermocouple.

Since only single point measurements are required in this invention and response times are below 0.1 s pyrometers can be used which typically detect the IR spectrum in the range of 2-20 μm. They are available pre-calibrated for a certain temperature range (e.g. 37±5° C.) and emissivity (i.e. 0.95 as for human skin). These instruments provide an absolute accuracy of better than 0.5° C. in the 10° C. range. The precision, i.e., the repeatability error for measurements under identical conditions is extraordinally small, typically in the range of 0.01° C. Temporal response is better than 10 Hz.

The absolute reading of a simple pyrometer is only correct if the emissivity of the inspected surface is known and the pyrometer is calibrated for this emissivity. The emissivity of human skin is about 0.95 as for most organic substances and does not vary appreciably with wavelength. Common IR detectors pre-calibrated for 0.95 are available.

IR Transparency of Clothes

Clothes are commonly made from polymers some of which are already relative IR transparent in the required range. However, especially polyethylene (C2H4)n is highly transparent to IR with only three narrow absorption maxima in the range of 2-20 μm. It is less commonly used for standard clothes. Still, it is proposed to design patient clothes preferredly made from polyethylene, potentially with some polyamide or polyester fiber content. An example of such clothes are labeled 402 in FIG. 4.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

100 magnetic resonance system
104 magnet
106 bore of magnet
108 measurement zone or imaging zone
110 magnetic field gradient coils
112 magnetic field gradient coil power supply
113 magnetic resonance imaging antenna
113' magnetic resonance imaging antenna
114 loop antenna element
114' loop antenna element
115 infrared thermometry sensor
115' infrared thermometry sensor
116 transceiver
118 subject
119 outer surface of subject
120 subject support
122 actuator
124 predetermined direction
125 slices
126 computer system
128 hardware interface
130 processor
132 user interface
134 computer storage
136 computer memory
140 pulse sequence instructions
142 magnetic resonance data
144 magnetic resonance image
146 thermometry data
148 predefined temperature or temperature model
150 control module
152 image reconstruction module
200 acquire the magnetic resonance data by controlling the magnetic resonance imaging system with the pulse sequence instructions
202 repeatedly measure at least one surface temperature of the subject with the multiple infrared thermometry sensors
203 decision box: is surface temperature above the predefined temperature?
204 perform a predefined action if the at least one surface temperature is above a predefined temperature 206 decision box: is the acquisition of magnetic resonance data finished?
208 end
300 magnetic resonance imaging system
302 support surface
400 enlarged view
402 infrared transparent garment
404 path
406 measurement point
600 current leads
602 central region
700 offset region

The invention claimed is:

1. A magnetic resonance imaging system for acquiring magnetic resonance data from a subject within an imaging zone, wherein the magnetic resonance imaging system comprises:
   a magnetic resonance imaging antenna comprising
      a plurality of loop antenna elements wherein the magnetic resonance imaging antenna further comprises multiple infrared thermometry sensors, wherein the magnetic resonance imaging antenna is configured for being positioned onto a portion of the subject and adjacent to an external surface of the subject, such that at least a portion of the multiple infrared thermometry sensors becomes directed towards the external surface when the magnetic resonance imaging antenna is positioned adjacent to the external surface of the subject;
   a memory containing machine executable instructions and pulse sequence instructions, and
   a processor for controlling the magnetic resonance imaging system, wherein execution of the machine executable instructions causes the processor to:
      acquire the magnetic resonance data by controlling the magnetic resonance imaging system with the pulse sequence instructions;
      repeatedly measure at least one surface temperature of the subject with the multiple infrared thermometry sensors during acquisition of the magnetic resonance data; and
      perform a predefined action if the at least one surface temperature is above a predefined temperature, for reducing the risk of the subject becoming overheated;
   wherein each of the plurality of loop antenna elements have current leads for feeding radio frequency currents into or receiving radio frequency currents from the loop antenna elements, wherein at least a subset of the multiple infrared thermometry sensors are positioned in an offset region offset from a center of the corresponding loop antenna element, wherein the current leads are within the offset region.

2. The magnetic resonance imaging system of claim 1, wherein the magnetic resonance imaging antenna is configured for functioning as a transmit antenna, wherein the magnetic resonance imaging system comprises a RF system for periodically supplying RF power to the loop antenna elements, wherein the loop antenna elements are disposed along the external surface of the subject, wherein the predefined action comprises reducing the RF power supplied to a loop antenna element in response to the corresponding infrared thermometry sensor measuring a surface temperature of the subject above the predefined temperature while continuing to acquire the magnetic resonance data.

3. The magnetic resonance imaging system of claim 1, wherein at least a portion of the multiple infrared thermometry sensors are pyrometers.

4. The magnetic resonance imaging system of claim 1, wherein the pulse sequence instructions generate pulse sequences modeled to keep induced temperatures within safety margins which increase scan time and wherein the processor is further configured to reduce the safety margins during generation of the pulse sequences to reduce scan time based on the measured surface temperatures.

5. The magnetic resonance imaging system of claim 1, wherein the magnetic resonance imaging antenna comprises a subject support configured for supporting the subject on a support surface at least partially within the imaging zone, wherein at least a portion of the antenna elements and the infrared thermometry sensors are arranged within the subject support with an infrared transmissive path being defined between the infrared thermometry sensors and temperature measurement points on a surface of the subject.

6. The magnetic resonance imaging system of claim 1, wherein the magnetic resonance imaging antenna includes capacitors and wherein the at least a subset of the multiple infrared thermometry sensors is disposed adjacent the capacitors.

7. The magnetic resonance imaging system of claim 1, wherein the magnetic resonance imaging system comprises an air cooling system for cooling the subject within the imaging zone with an air flow, wherein the predefined action comprises increasing the air flow if the at least one surface temperature is above the predefined temperature.

8. The magnetic resonance imaging system of claim 1, wherein execution of the machine executable instructions further causes the processor to select the predefined temperature from a table of predefined temperatures using any one of the following criterion: subject weight, subject age, subject type, subject size, and combinations thereof.

9. The magnetic resonance imaging system of claim 1, further including:
   an infrared transparent fabric material disposed between the external surface of the subject and the infrared thermometry sensors.

10. A magnetic resonance imaging system for acquiring radio frequency (RF) magnetic resonance data from a three-dimensional (3D) imaging zone within a subject, wherein the magnetic resonance imaging system comprises:
   a surface magnetic resonance imaging radio frequency (RF) antenna comprising a plurality of loop RF antenna elements, wherein the magnetic resonance imaging RF antenna includes a plurality of infrared thermometry sensors, wherein the magnetic resonance imaging RF antenna is configured to be positioned onto a portion of the subject and adjacent and at least partially conform to an external surface of the subject to receive the RF magnetic resonance data from the 3D imaging zone within the subject, such that at least a portion of the plurality of the infrared thermometry sensors are directed towards the external surface of the subject when the magnetic resonance imaging antenna is positioned adjacent to the external surface of the subject with the loop RF antenna elements generally parallel to the external surface, wherein each of the plurality of loop antenna elements have current leads for feeding radio frequency currents into or receiving radio frequency currents from the loop antenna elements, wherein at least a subset of the multiple infrared thermometry sensors are positioned in an offset region offset from a center of the corresponding loop antenna element, wherein the current leads are within the offset region;
- a computer processor configured to control the magnetic resonance imaging system to:
  - acquire the RF magnetic resonance data by controlling the magnetic resonance imaging system with pulse sequence instructions;
  - repeatedly measure surface temperature of the subject with the plurality of infrared thermometry sensors during the acquisition of the RF magnetic resonance data; and
  - based on the measured surface temperature, modify the pulse sequence instructions during the acquisition of the RF magnetic resonance data to accelerate the acquisition of the magnetic resonance data.

11. A method of operating a magnetic resonance imaging system for acquiring magnetic resonance data from a subject within an imaging zone, wherein the magnetic resonance imaging system comprises a magnetic resonance imaging antenna comprising a plurality of antenna elements, wherein each of the antenna elements is a loop antenna element, wherein the magnetic resonance imaging antenna further comprises multiple infrared thermometry sensors, wherein the magnetic resonance imaging antenna is positioned onto a portion of the subject and adjacent to an external surface of the subject, wherein at least a portion of the multiple infrared thermometry sensors are directed towards the external surface when the magnetic resonance imaging antenna is positioned adjacent to the external surface with at least a subset of the loop antenna elements parallel to the external surface, wherein each of the plurality of loop antenna elements have current leads for feeding radio frequency currents into or receiving radio frequency currents from the loop antenna elements, wherein at least a subset of the multiple infrared thermometry sensors are positioned in an offset region offset from a center of the corresponding loop antenna element, wherein the current leads are within the offset region, wherein the method comprises the steps of:
- acquiring the magnetic resonance data by controlling the magnetic resonance imaging system with pulse sequence instructions;
- repeatedly measuring a surface temperature of the subject with the multiple infrared thermometry sensors during acquisition of the magnetic resonance data; and
- performing a predefined action based on the surface temperature.

12. The method of claim 11, wherein the method further comprises placing an infrared transparent garment on the outer surface of the subject before acquiring the magnetic resonance data.

13. The method of claim 12, wherein the infrared transparent garment is fabricated at least partially from polyethylene foil.

14. The method of claim 11, wherein the predefined action includes reducing a risk of a subject becoming overheated and wherein the predefined action is performed in response to the external surface temperature of the subject being above a predefined temperature.

15. The method of claim 11, wherein the pulse sequence instructions generate pulse sequences modeled to keep induced temperatures within safety margins which safety margins increase scan time and further including adjusting the safety margins based on the measured surface temperatures by increasing power to the antenna elements to reduce scan time.

16. A magnetic resonance imaging antenna comprising a plurality of antenna elements, wherein each of the antenna elements is a loop antenna element, wherein the magnetic resonance imaging antenna further comprises a plurality of infrared thermometry sensors, wherein the magnetic resonance imaging antenna is configured for being positioned adjacent to an external surface of the subject, wherein at least a portion of the multiple infrared thermometry sensors are directed towards the external surface when the magnetic resonance imaging antenna is positioned adjacent to the external surface;
- wherein the magnetic resonance imaging antenna is flexible and wherein the loop antenna elements each include leads for feeding radio frequency currents into or receiving radio frequency currents from a corresponding loop antenna element, at least one of the leads and the loop antenna elements being interrupted by capacitors, at least a subset of the infrared thermometry sensors being disposed offset from a center of a corresponding loop antenna element adjacent the capacitors and configured to measure temperature at measurement points on the external surface of the subject adjacent the capacitors.

17. The magnetic resonance imaging antenna of claim 16, wherein the magnetic resonance imaging antenna is integrated into a subject support.

18. A magnetic resonance imaging system for acquiring magnetic resonance data from a subject within an imaging zone, wherein the magnetic resonance imaging system comprises:
- a magnetic resonance imaging antenna comprising a plurality of loop antenna elements and the magnetic resonance imaging antenna further comprises multiple infrared thermometry sensors, wherein the magnetic resonance imaging antenna is configured for being positioned onto a portion of the subject and adjacent to an external surface of the subject such that at least a portion of the multiple infrared thermometry sensors are disposed adjacent and directed towards the external surface of the subject when the magnetic resonance imaging antenna is positioned adjacent to the external surface of the subject to sense infrared radiation emanating from measurements on the external surface of the subject, wherein each of the plurality of loop antenna elements have current leads for feeding radio frequency currents into or receiving radio frequency currents from the loop antenna elements, wherein at least a subset of the multiple infrared thermometry sensors are positioned in an offset region offset from a center of the corresponding loop antenna element, wherein the current leads are within the offset region;
- a processor configured to control the magnetic resonance imaging system to:
  - acquire the magnetic resonance data from the subject using magnetic resonance sequences that induce heating in the subject,
  - repeatedly measure surface temperatures of the subject at the measurement points with the multiple infrared thermometry sensors during acquisition of the magnetic resonance data, and
  - in response to surface temperatures at one or more of the measurement points being below heating limits during acquisition of the magnetic resonance data, recalculating the magnetic resonance sequences to shorten magnetic resonance data acquisition times.

* * * * *